US007778434B2

(12) United States Patent
Juneau et al.

(10) Patent No.: US 7,778,434 B2
(45) Date of Patent: Aug. 17, 2010

(54) SELF FORMING IN-THE-EAR HEARING AID WITH CONICAL STENT

(75) Inventors: Roger P. Juneau, Destrehan, LA (US); Edward J. Desporte, Covington, LA (US); Michael Major, Mandeville, LA (US); Gregory R. Siegle, Metairie, LA (US); Brian Tanner, Destrehan, LA (US)

(73) Assignee: General Hearing Instrument, Inc., New Orleans, LA (US)

( * ) Notice: Subject to any disclaimer, the term of this patent is extended or adjusted under 35 U.S.C. 154(b) by 338 days.

(21) Appl. No.: 11/627,714

(22) Filed: Jan. 26, 2007

(65) Prior Publication Data
US 2007/0183613 A1 Aug. 9, 2007

Related U.S. Application Data

(63) Continuation-in-part of application No. PCT/US2005/019046, filed on May 31, 2005, and a continuation-in-part of application No. 11/138,540, filed on May 26, 2005, now abandoned.

(60) Provisional application No. 60/575,533, filed on May 28, 2004, provisional application No. 60/762,429, filed on Jan. 26, 2006, provisional application No. 60/825,988, filed on Sep. 18, 2006.

(51) Int. Cl.
*H04R 25/00* (2006.01)
(52) U.S. Cl. .................. 381/328; 381/322; 381/330
(58) Field of Classification Search .................. 381/312, 381/322, 328, 330
See application file for complete search history.

(56) References Cited

U.S. PATENT DOCUMENTS

| 3,865,998 | A | | 2/1975 | Weiss et al. |
| 4,291,203 | A | * | 9/1981 | Bellafiore .................. 381/328 |
| 4,539,440 | A | | 9/1985 | Sciarra |
| 4,762,135 | A | | 8/1988 | van der Puije et al. |
| 5,008,058 | A | * | 4/1991 | Henneberger et al. ....... 264/134 |
| 5,630,839 | A | | 5/1997 | Corbett, III et al. |
| 5,772,575 | A | | 6/1998 | Lesinski et al. |
| 5,800,500 | A | | 9/1998 | Spelman et al. |
| 5,977,689 | A | | 11/1999 | Neukermans |
| 5,999,859 | A | | 12/1999 | Jolly |

(Continued)

*Primary Examiner*—Suhan Ni
*Assistant Examiner*—Jasmine Pritchard
(74) *Attorney, Agent, or Firm*—Garvey, Smith, Nehrbass & North, L.L.C.; Seth M. Nehrbass; Charles C. Garvey, Jr.

(57) ABSTRACT

A hearing aid body is provided that contains electronic hearing aid components and that is attachable to the user's body outside the ear canal. A conduit connects the hearing aid body to the flexible plug. The conduit enables sound emitted by the hearing aid to travel via the conduit to the flexible plug so that the user's able to hear a sound that is amplified by the hearing aid and received by the plug via the conduit. The conduit can be a flexible hollow tube or an electronic conduit that transmit electrical signals between the hearing aid and the plug. A stent embedded in the plug is provided, the stent having a first smaller diameter at a temperature below body temperature and being expandable to a second greater diameter when subjected to the user's body temperature, such as the temperature in the ear canal of a user.

13 Claims, 11 Drawing Sheets

U.S. PATENT DOCUMENTS

| | | |
|---|---|---|
| 6,135,235 A | 10/2000 | Brimhall |
| 6,153,966 A | 11/2000 | Neukerman et al. |
| 6,478,656 B1 | 11/2002 | Khouri |
| 7,362,875 B2 * | 4/2008 | Saxton et al. ............... 381/322 |
| 2002/0129819 A1 | 9/2002 | Feldman et al. |
| 2002/0196958 A1 | 12/2002 | Halteren et al. |
| 2004/0165742 A1 | 8/2004 | Shennib et al. |
| 2004/0215053 A1 * | 10/2004 | Jorgensen et al. ............. 600/25 |
| 2004/0258263 A1 | 12/2004 | Saxton et al. |

* cited by examiner

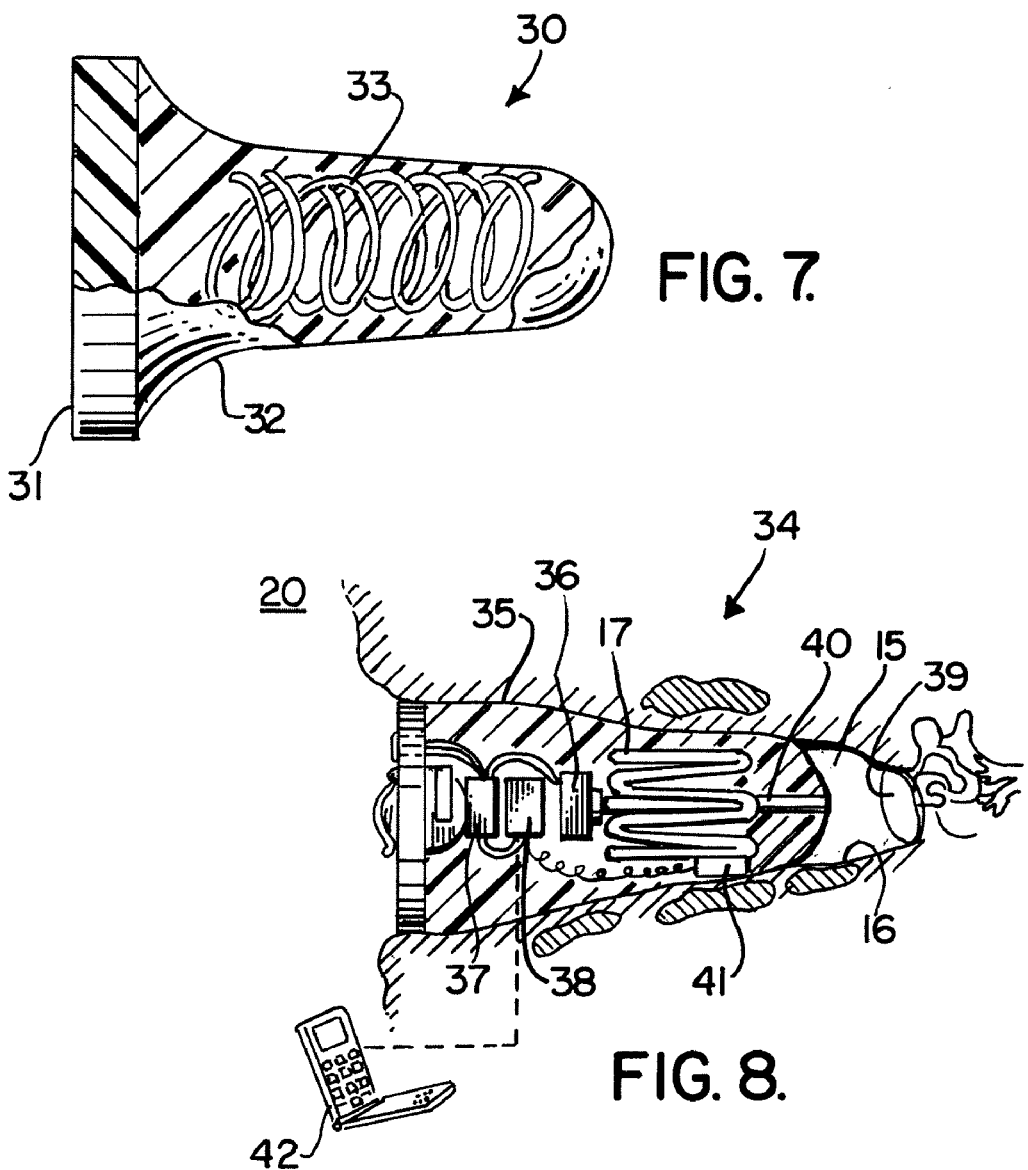
FIG. 7.
FIG. 8.
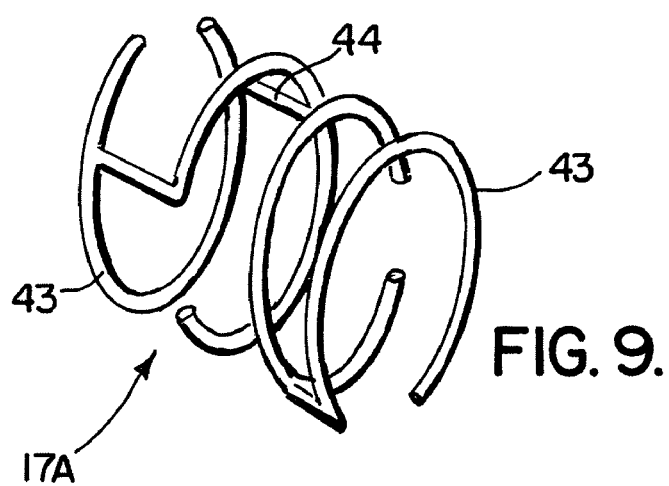
FIG. 9.

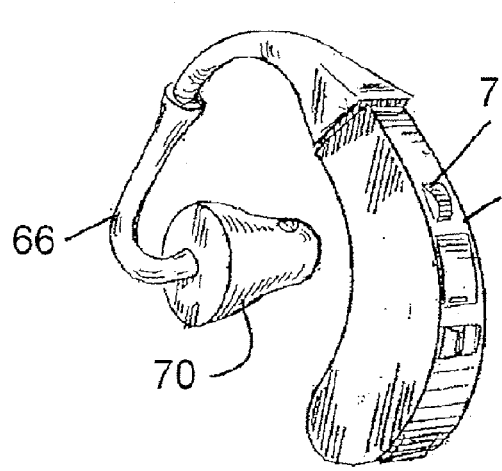
FIG. 24
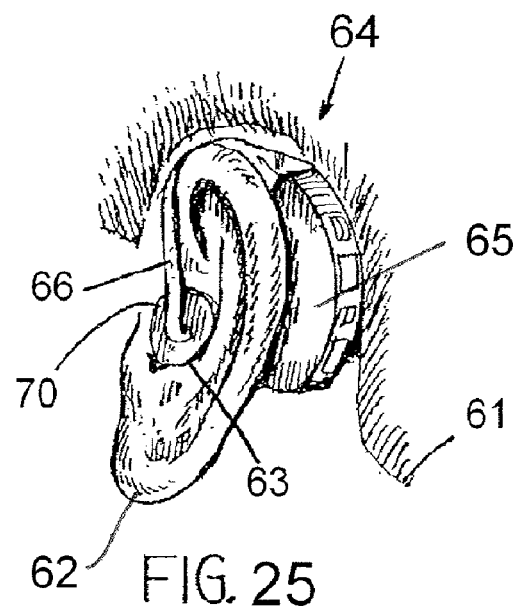
FIG. 25
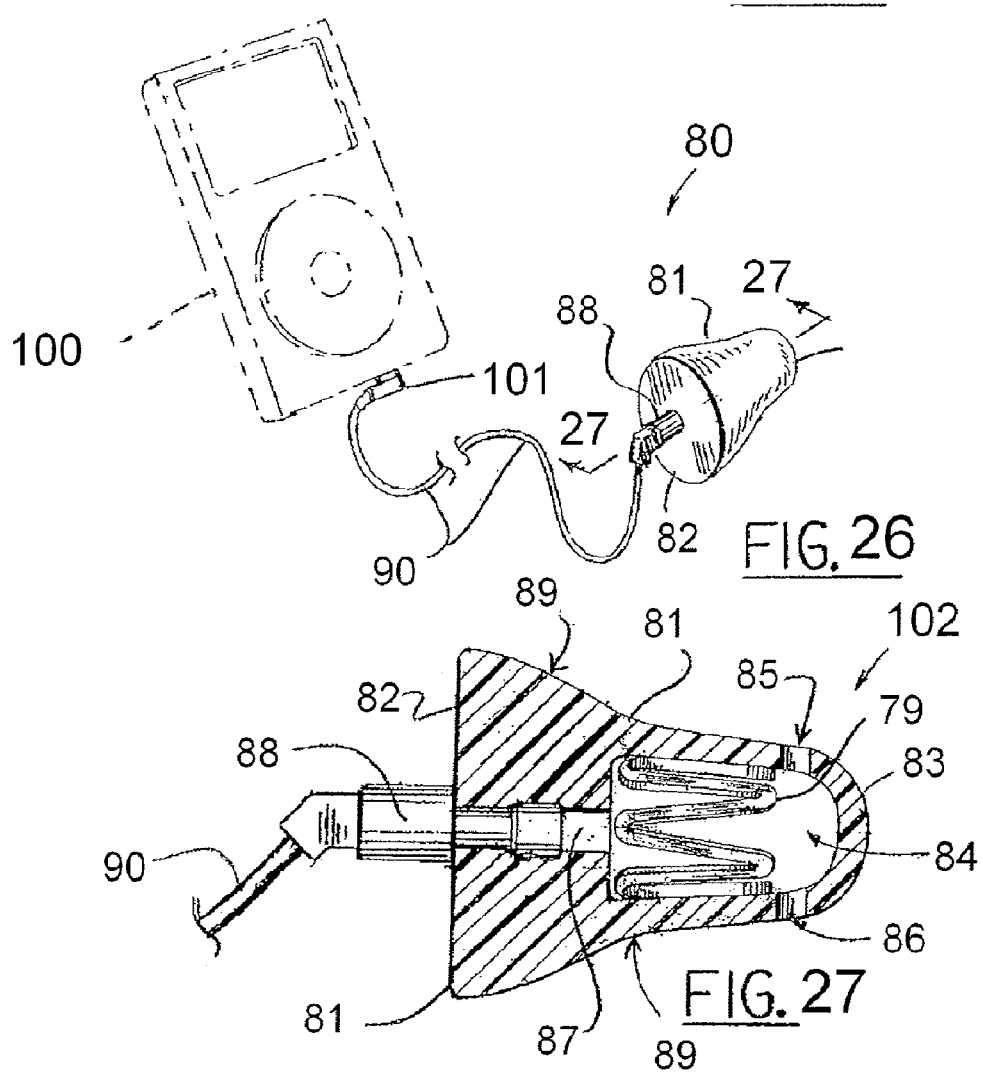
FIG. 26
FIG. 27

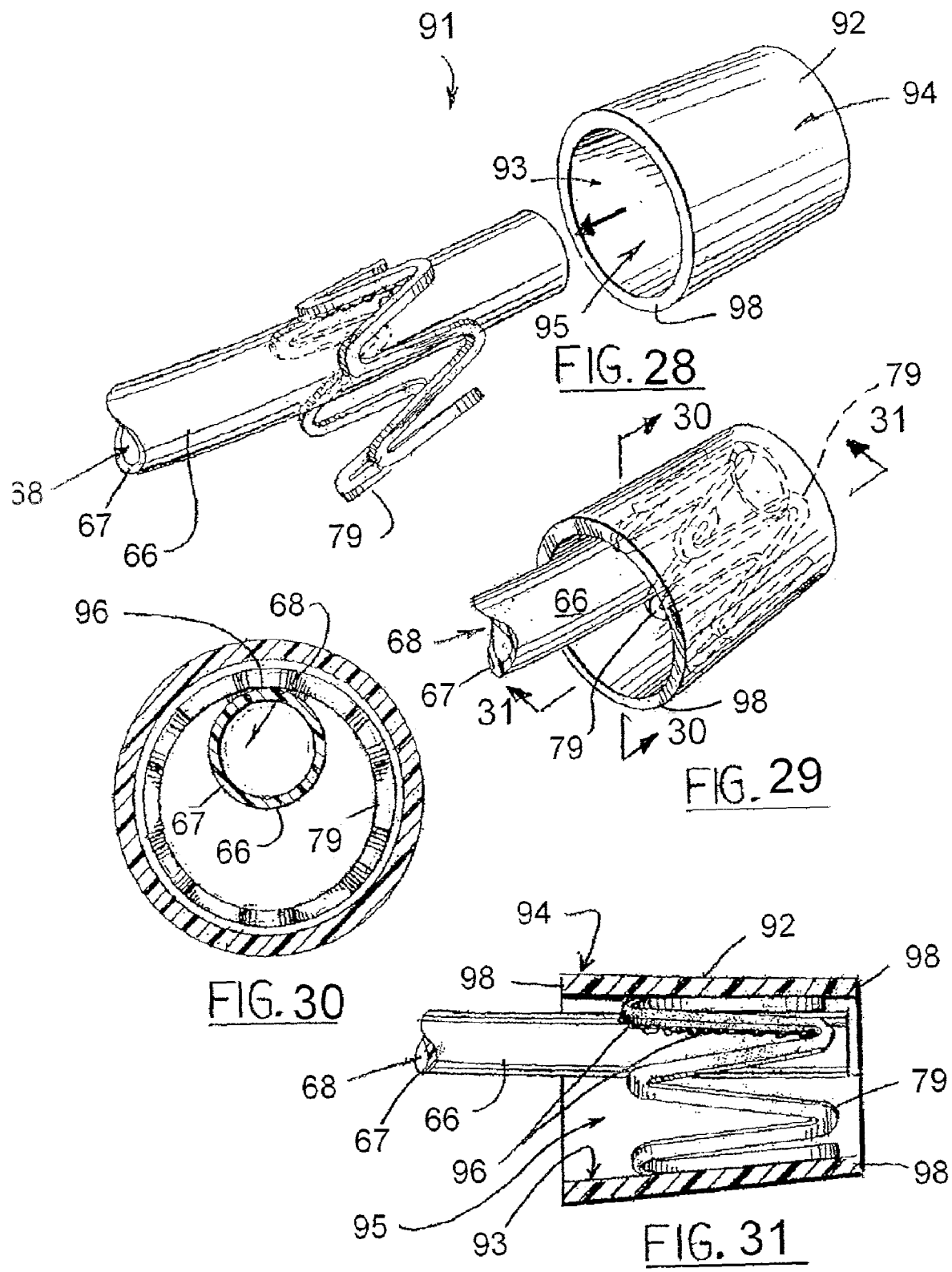

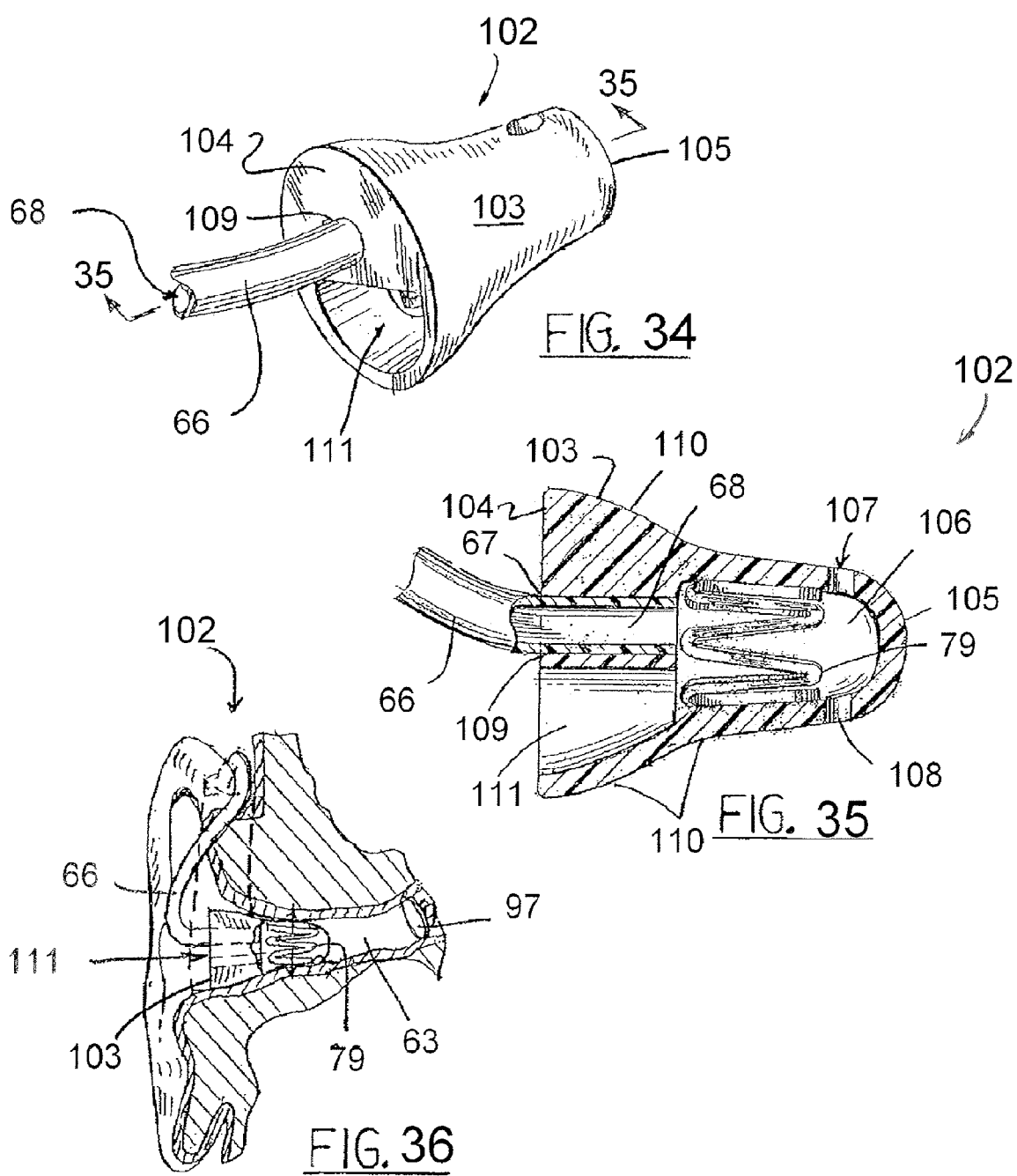

SELF FORMING IN-THE-EAR HEARING AID WITH CONICAL STENT

CROSS-REFERENCE TO RELATED APPLICATIONS

Incorporated herein by reference are our U.S. Provisional Patent Application No. 60/762,429, filed 26 Jan. 2006, and our U.S. Provisional Patent Application No. 60/825,988, filed 18 Sep. 2006, priority of both of which is hereby claimed.

Incorporated herein by reference are our International Application No. PCT/US2005/019046, filed 31 May 2005 (and re-published on 16 Mar. 2006 as International Publication No. WO 2005/120131 A2), our U.S. patent application Ser. No. 11/138,540, filed 26 May 2005 (published as US 2006-0098833 A1 on 11 May 2006), and our U.S. Provisional Patent Application No. 60/575,533, filed 28 May 2004.

In the US, this is a continuation-in-part of International Application No. PCT/US2005/019046, filed 31 May 2005 and of U.S. patent application Ser. No. 11/138,540, filed 26 May 2005 now abandoned. In the US, priority of U.S. Provisional Patent Application No. 60/575,533, filed 28 May 2004, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to hearing devices. More particularly, the present invention relates to in-the-canal hearing devices, wherein a metallic frame expands responsive to body temperature when inserted into the ear canal to ensure a good fit.

The present invention relates to hearing aids and more particularly to an improved hearing aid that utilizes an expandable plug that fits the ear canal of a wearer, the plug carrying a nitinol stent that expands in response to a temperature increase caused by human body temperature, a provided cable (e.g. tube or enabling wire) a connection to be formed between the plug and a hearing aid device (mounted on the outer ear or on a wearer's belt, for example).

2. General Background of the Invention

The hearing industry has desired a one size fits most ear piece to efficiently serve the hearing impaired for many years. Industrial audiologists have also advocated a one-size-fits-most to serve in the hearing protection and communication needs in industry, sport shooting, and military applications. This device has eluded engineers and researchers because the human ear canal is dynamic in nature and is anatomically variant between subjects (indeed, variant from ear to ear).

Each ear canal shape is unique in size, in the directional bend into the head, in geometrical shape (i.e., circular vs. elliptical cross section), and in sensitivity to contact pressure (in the form of a plugged up feeling, in sensations pain, or in reactions of coughing or sneezing). These anatomical variations are a fit problem in combination with dynamic action of the ear canal caused by the rolling, medial to lateral motion of the temperomandibular joint (TMJ) during the opening closing one's mouth. Research has demonstrated that dynamic action of the anterior-posterior plane of the ear canal will vary by about three to five millimeters during talking, chewing, or laughing. These factors, along with the fact that the ear canal slopes upward along the medial plane, deleteriously affect efforts to maintain an acoustic seal in the external ear canal in normal, daily operation of a hearing device.

The challenge to one-size-fits-most is heightened by the secretions of cerumen, oils, and moisture impeding electronic performance and life cycle. The chemical make up of cerumen alone is as individual as the ear in which the end product will reside. Cerumen may vary in acidity, as well as in the content of lipids, proteins, cholesterols, and waxy esters. The content latter component will, in fact, determine whether a wearer's cerumen is "wet" or "dry" in nature, each of which presents a different problem for hearing instrument longevity.

From a psycho-acoustic perspective the location and pressure of the acoustic seal is very important. Poor placement will cause a sense of occlusion or stuffiness in the ear. The occlusion effect is the result of soft-tissue-conducted sounds that create an internal sound level greater than 10-12 dB above the ambient (or "out-side" of the head) sound levels. When this occurs, wearers report their own voices sounding funny, hollow, or as if their heads are in barrels. This is commonly caused by too tight an acoustic seal on soft tissue between the aperture medially to the first directional bend of the external ear canal. Occlusion effect is further heightened by varied peripheral or "slit leakage" and poor or no venting. The slit leakage facilitates annoying low frequency resonation and distorts the mid-frequency sounds. Conversely, these problems are best managed with good venting and uniform acoustic seal.

When the acoustic seal is created properly at a point in the ear canal where there is a balance of cartilaginous and bony material, there is less slit leakage, sound is natural, and acoustic feedback is avoided. By adding a well designed vent system to allow excess low frequency sound energy to roll-off, and undesireably high ear canal air pressure to be released, the hearing device is optimized in all applications. The over-all performance of the device can then yield better sound quality and "distinctness of sounds."

With the goal of high fidelity amplification in both custom and non-custom hearing instruments, entailing a 20-20,000 Hz frequency response, a dynamic, secure, yet comfortable acoustic seal is paramount.

All previous efforts to achieve this type of fit have revolved around the concept of building up the exterior of the hearing instrument, making a "tighter" fit. This approach, unfortunately, was the only avenue available with those instruments composed of rigid, non-compliant acrylic.

The traditional shell molded from an individual's unique ear impression has not yielded a truly typical form that anatomically fits a significant percentage of any external ear category. It is further limited by a dated acrylic design which is the most commonly used shell technology. This technology was adopted from dental industry in the 1960's. It has a Shore Hardness factor of 90 Durometer. Little design change has been introduced since its development. Production and curing techniques have improved, however, through laser modeling and 3-D imaging. Since the ear is a dynamic acoustic environment and is ill-served by a rigid material like acrylic. The material however has a reasonable life cycle in the environment of the ear. Hard Durometer devices rock in the ear with jaw motion (TMJ), as opposed to flexing and accommodating the dynamic action of the ear.

Attempts with soft hollow shell technology have failed based on several key issues: Most soft material shrinks, discolors (usually unsightly yellow or brown), hardens after a few months.

Silicone based materials, which are preferred to be used in the body, are incompatible for bonding to the typical electronic faceplate. Soft/hollow materials tend to collapse upon insertion and deform over time loosing their ability to create an acoustic seal.

Foam technology typically requires multiple sizes to achieve a fit. They are uncomfortable, stuffy, and should not be reused as cellular foam becomes a breeding ground for bacteria.

Hearing aids are supplied in many types and configurations. One example of a hearing aid is the common behind-the-ear or "BTE" style hearing aid that hooks upon the outside surface of a user's ear. Another type of hearing aid is an in-the-ear type hearing aid that is entirely contained within the ear canal of a wearer. With the in-the-ear style hearing aid, an external plate is mounted at the outer surface of the ear and providing controls for enabling the wearer to change the volume of the hearing aid.

Some people do not like the in-the-ear style hearing aid. Some users have the degree of hearing loss where beneficial gain before feedback cannot be achieved with traditional in-the-ear hearing aids. Other users dislike the appearance of those custom fit in-the-ear hearing aids, and find them very unattractive. Still others find that in-the-ear hearing aids are prone to cerumen-related failures requiring frequent repairs. Others prefer the larger electronics package that can be placed in a behind-the-ear type hearing aid. BTE hearing aids generally provide much more power before feedback. They also, because of increased size, offer more features (e.g. frequency shaping potentiometers). They can also prove to be easier to adjust for those users with impaired dexterity. In addition, and also because of their size, BTE hearing aids are amenable to interfacing with assistive listening devices, and with communication devices. Finally, BTE devices rarely fail because of cerumen; the cerumen is accreted in the ear mold, which is usually easy to clean.

The following US patents are each hereby incorporated herein by reference:

U.S. Pat. No. 6,478,656 Method and apparatus for expanding soft tissue with shape memory alloys; This patent describes the application of a body worn bra where by the soft tissue of the skin forming the breast is expanded by incorporating an adhesive and an appliance with a shape memory alloy.

U.S. Pat. No. 6,135,235 discloses a self-cleaning cerumen guard for a hearing device.

U.S. Pat. No. 5,999,859 discloses a apparatus and method for perimodiolar cochlear implant with retro-positioning.

U.S. Pat. No. 5,977,689 discloses a biocompatible, implantable hearing aid microactuator.

U.S. Pat. No. 5,800,500 discloses a cochlear implant with shape memory material and method for implanting the same.

U.S. Pat. No. 5,772,575 discloses an implantable hearing aid.

U.S. Pat. No. 5,630,839 discloses a multi-electrode cochlear implant and method of manufacturing the same.

U.S. Pat. No. 4,762,135 discloses a cochlea implant.

U.S. Pat. No. 3,865,998 discloses an ear seal. This patent states that the typical cross section of the external ear canal is best approximated by a super ellipse which is defined by the equation: $(x/a)^n + (y/b)^n = 1$ where $n=2.4$. The hypothesis is that an ear seal could be created using a soft material with an outer periphery defined by the super elliptic shape. The patent does not address the bigger issues associated with the longitudinal axes formed by extending a line through the medial-lateral plane or the dynamic nature of the TMJ. The latter issue was neglected because the device was very short by today's standards for insertion. The patent also did not consider the surface pressure necessary to create the acoustic seal it desired to deliver. In essence it was a tapered flanged silicone plug of super ellipse cross section.

Incorporated herein by reference are all patent applications and patents naming one or more of us as inventors.

Nitinol wire is used in a variety of medical and nonmedical device applications including guide wires, catheters, stents, filters, orthodontic appliances, eyeglass frames, cellular phone antennae and fishing tackle, to name a few.

Because shape memory and super elasticity are very temperature dependent, the fully annealed austenitic peak temperature is used to classify Nitinol to set the transformation temperature at which the Nitinol material has completely transformed to its memory shape or below which, exhibits malleable, ductile characteristics.

Of the many mechanical properties unique to Nitinol, two critical characteristics exhibited in the austenitic phase are the loading plateau and the unloading plateau, usually diagrammed on a stress/strain curve. The loading plateau is the stress level at which material produces an almost constant stress level over a relatively large range of strain, up to about 8%. Stainless steel conversely, does not exhibit this property of constant stress after 0.3% of strain. Other information relating to Nitinol can be found at www.nitinol.com.

BRIEF SUMMARY OF THE INVENTION

The present invention provides a unique self-forming device to the individual external ear canal employing a metallic frame, preferably of the Nitinol family of alloys. The current preferred Nitinol is comprised of near equiatomic percentages of nickel and titanium, such as Memry Corporation tube stock BB-196×230.

Nitinol exhibits a thermoelastic transformation. This transformation is responsible for either shape memory or super elasticity being exhibited by the alloy on the respective side of the target temperature. Following deformation below the transformation range, the property called "shape memory" allows recovery of a predetermined shape upon heating above the transformation range. Super elasticity is the non-linear recoverable deformation behavior at temperatures above the austenitic finish (Af) temperature, which arises from the stress-induced martensitic transformation on loading and the reversion of transformation upon unloading. Coronary stents utilize this technology as a recovery mechanism once deformed and inserted through a catheter. The Nitinol alloy is strong and resilient. The strain recovered with shape memory or super elasticity typically provides nearly ten times the elastic spring back of other alloys such as stainless steel. Additionally, Nitinol has excellent biocompatibility properties.

The austenitic and martensitic characteristics of a Nitinol endoskeleton, in concert with a soft-solid silicone body, act to create an easily inserted ready-wear ear device that will self-form to the shape of the external ear canal, establishing a precise wall pressure. Simply stated, a small soft device with the endoskeleton grows once inserted into the ear canal. It may transform by heat, electrical current, or other means. As it grows (i.e. recovers from deformation to the pre-molded shape) to sufficient size, the ear worn device resides in equilibrium, comfortably and securely in the ear. The endoskeleton can be shaped similar to a human rib cage. This anatomical choice allows the device to expand like the chest cavity breathing. The particular design more closely follows that of an eel or snake rib cage. This makes the instrument self-seeking during insertion as it snakes through the directional bends of the ear canal.

The present invention also provides a hearing device or hearing aid or hearing protector with a Nitinol endoskeleton in a soft silicone body that will enhance the fitting of pediatric and young children, who have been relegated to wearing behind-the-ear appliances that are routinely taped to the heads of the young wearers. In the past, parents have objected to this practice, but are typically faced with no alternatives. Small in-the-ear hearing devices can, with this invention, be manufactured with an endoskeleton, extending the proper fit of the device by several months. This enables the commercialization of a new generation hearing device uniquely suited for children. Today, children outgrow acrylic devices. They are often outgrown too quickly to be cost effective.

Advanced self-forming endoskeleton technology will eventually achieve a customer satisfaction ratings of 80-90%. Advances in shell technology incorporating soft-solid bodies with endoskeletons manufactured from memory-metal technology will make it possible to mass-produce instruments that will provide a secure, comfortable fit rivaling custom-fit instruments. This will result in better over-all sound performance and cost reductions based on mass production techniques. Significant savings will be realized at all levels of the current hearing aid delivery system. The need to make ear impressions will be greatly reduced, eliminating the need to send those impressions into a laboratory. In those cases where ear impressions are necessary, the application of shape memory technology will yield a more predictable fit in the custom-molded embodiment.

Post-fitting care will be greatly improved in that a replacement or loaner device is readily available to the patient. This alone will reduce office visits for the patient and eliminate overnight delivery cost necessary to meet patient expectations on an important medical, audio, or communications device.

To this end, this shape memory technology will lead to impression-less hearing aids for the vast majority of the hearing impaired market. Ready wear fittings will achieve levels of fit, comfort, security, and performance that will rival or exceed custom devices. These improvements will affect all devices intended to be inserted into the ear for sound delivery and voice pickup.

Voice-pickup technology, through the use of subminiature electret microphones, piezoelectric accelerometers (similar to the Endevco Model 22 PICOMIN™), or MEMS accelerometers, facilitates communication through hard wired or wireless platforms such as Blue Tooth or Zigbee. In turn, the acoustic system delivers incoming signals to the ear drum. For voice-pickup, the accelerometer is positioned between the external ear canal wall and the outer side of the stent in such a way as to create radial pressure between the ear canal and the accelerometer. This design could achieve hands free communication in many applications.

The design of a self-forming device is achieved by expanding the soft-solid device in a way that contact with the external ear canal wall is achieved by reaching equilibrium. Each surface point on the external ear canal wall, adjacent to the skeletal structure, will have forces on the canal wall where, $F(a)=F(b)=F(c)=F(n)$. The shape of the extruded wire may be, for example, round or rectangular or of an I-beam cross-section. The cross-sectional shape and the cross sectional area of the members forming the endoskeleton, such as a stent or truss system, govern the amount of force that the endoskeleton will exert on the silicone embedding it. This force, by design, is equal to the elasticity of the surrounding silicone plus the required surface pressure necessary to bring the external surface of the device into contact with the wall of the external ear canal. This will establish an acoustic seal of known pressure. This, in turn, will accommodate a variety of ear canal shapes within the known range of deflection. This self regulating force will enable custom-molded devices to fit optimally and will enable ready-wear devices to accomplish one-size-fits-most in real world terms. The forces generated by the endoskeleton will be perpendicular to the ear canal wall, eliminating any shearing action on the skin.

The mechanics of the current device are driven by temperature change from room temperature to ear canal temperature. In another embodiment, the transformation is driven by an electrical current through the endoskeleton. This could be necessary in applications where room temperature is greater than ear canal temperature. Activation temperatures are metallurgically set.

The following are exemplary endoskeleton material parameters for the memory metal (Nitinol, from Fort Wayne Metals Research Corporation):

1. Passive metal excited by temperature change:
   i. EAC temperature @ 35° C.±1° C.
   ii. T=10° C.±1° C. or 32° C.±3° C.
2. Active metal excited by an electrical current.
   i. Electrical current will heat the Nitinol, causing transformation.
3. Attribute of Nitinol:
   i. Will not interfere with hardware of wireless communication.

The endoskeleton extruded design can be a simple spring. The intended use is to pull on the proximal end of the device, there by reducing its cross sectional area and increasing its longitudinal dimension. Once inserted, the device returns the device to a diameter sealing the ear canal with uniform pressure. The Nitinol is molded as a star in its austenitic. The intended use is to compress the proximal end of the device on the endoskeleton, thereby reducing its cross sectional area. As the user inserts the device, its memory shape returns the device to a diameter sealing the ear canal with uniform pressure. A gradient wedge coil can be formed from extruded wire, molded into a coil with the thicker end to be placed near lateral end. A truss system can include members of cross-sectional shapes selected to optimize the deflection and force transferred to the ultimate excursion of the silicone device. The truss system shape is selected to accommodate a typical ear canal shape. Sinusoidal shapes of various cross-sectional sizes can be connected together to generate vector forces of precise angular change delivering optimum excursion of the endoskeleton. These designs are generally micro-machined from tubing, laser cut, and micro blasted to a polished finish.

The endoskeleton would ideally be of a shape to optimize acoustic seal, placed in the device to minimize the occlusion effect. The acoustic seal would be uniform on the canal wall three millimeters past the second directional bend. In power hearing device applications, the seal could be continuous from the aperture to three millimeters past the first directional bend.

The endoskeleton would also serve to further protect the delicate electronics.

The present invention also provides an improved hearing aid that features a flexible plug that is sized and shaped to fit a user's ear canal. A stent is contained within, carried by or embedded in the plug, the stent having a first smaller diameter at a first temperature below body temperature and being expandable to a second greater diameter when subjected to a user's body temperature such as when placed in the ear canal of the user.

A hearing aid body containing an electronic hearing aid component or components (or a sound generating device) is attachable to the user's body outside the ear canal. The sound generating device can be a hearing aid, any music player (e.g. MP3 player, CD player, ipod®, Walkman®, radio, or the like), or any electronic communication device (e.g. Walkie-Talkie, radio, police or governmental communication device. A conduit connects the hearing aid body (or other sound generating device) and the plug, the conduit enabling sound emitted by the hearing aid body (or sound generating device) to travel via the conduit to the flexible plug, thus enabling the user to hear the sound received by the plug that occupies the user's ear canal.

The conduit can be a flexible tube in one embodiment, such as an elongated hollow flexible tube constructed of polymeric material, plastic, rubber or the like.

In another embodiment, the conduit is an electronic conduit that interfaces a electronic hearing aid device or component contained in the hearing aid body and a second electronic component carried by the plug. The stent can be a nitinol stent The stent can be generally cylindrically shaped. The stent can be of a wire frame construction.

The plug can be of a polymeric material. The plug can be of a silicone material.

In the preferred embodiment, the hearing aid body provides a speaker and the conduit affixes to the hearing aid body next to the speaker, wherein the conduit is an elongated tube with a hollow bore for carrying sound between a speaker contained in the hearing aid body and the plug.

In one embodiment, the plug carries an electronic component, preferably a speaker and a wire interfaces the speaker with other hearing aid components contained in a separate hearing aid body. The speaker can be easily detachable from the plug.

In another embodiment, the stent is carried by an open ended tubular plug having a lumen or bore that enables sound to travel via air to the user's ear drum. In this latter embodiment, the user is able to hear certain frequency sounds via the open ended bore while a conduit transmits certain frequency sounds that the user would not normally hear.

A soft-solid ear piece is formed to fit the typical human ear canal and will self form to fill the ear cavity by having an internal structure, endoskeleton, or bladder to expand to precisely fit the ear piece securely and comfortably in the ear canal. A nitinol metallic skeleton is embedded in the ear piece. The skeleton can have a tapered or a frustoconical shape. This self forming ear piece will enable ready-wear and custom molded hearing aids, hearing protectors, audio ear pieces, cell phone ear pieces and assistive listening devices to fit comfortably, securely, and free of acoustic feedback in the external ear canal. It creates an acoustic seal to optimally reduce peripheral leakage and intermodulation distortion delivering excellent acoustic performance while keeping environmental sounds blocked out. In another embodiment, a hearing aid provides a flexible plug that is sized and shaped to fit a user's ear canal. A stent embedded in the plug is provided, the stent having a first smaller diameter at a temperature below body temperature and being expandable to a second greater diameter when subjected to the user's body temperature, such as the temperature in the ear canal of a user. A hearing aid body is provided that contains electronic hearing aid components and that is attachable to the user's body outside the ear canal. A conduit connects the hearing aid body to the flexible plug. The conduit enables sound emitted by the hearing aid to travel via the conduit to the flexible plug so that the user's able to hear a sound that is amplified by the hearing aid and received by the plug via the conduit. The conduit can be a flexible hollow tube. The conduit can be an electronic conduit such as a wire or wires that transmit electrical signals between the hearing aid and the plug. In the second embodiment, the plug can contain a hearing aid component such as a speaker.

BRIEF DESCRIPTION OF THE DRAWINGS

For a further understanding of the present invention, reference should be had to the following detailed description, read in conjunction with the following drawings, wherein like reference numerals denote like elements and wherein:

FIG. 7 is a side sectioned view of the preferred embodiment of the apparatus of the present invention showing a Nitinol skeleton as a spring;

FIG. 8 is a side, sectioned view of the preferred embodiment of the apparatus of the present invention showing the Nitinol stent in the Austenite finish, wherein the expanded size creates pressure on an accelerometer, establishing a vibratory pathway from the ear canal wall so that the accelerometer picks up vibratory voice signals from the wearer to be transmitted to a communication device by a hard wire or a wireless system;

FIG. 9 is a perspective view of the preferred embodiment of the apparatus of the present invention showing a Nitinol stent characterized by rotating horseshoe cross sections that are in the molded state at the Austenite finish, (the expanded size when in the device of FIG. 3);

FIG. 24 is a perspective view of the second embodiment of the apparatus of the present invention;

FIG. 25 is a perspective view of the second embodiment of the apparatus of the present invention;

FIG. 26 is a perspective view of a third embodiment of the apparatus of the present invention;

FIG. 27 is a sectional view of a third embodiment of the apparatus of the present invention;

FIG. 28 is a perspective view of a fourth embodiment of the apparatus of the present invention;

FIG. 29 is a perspective view of a fourth embodiment of the apparatus of the present invention;

FIG. 30 is a sectional view taken along lines 30-30 of FIG. 29;

FIG. 31 is a sectional view taken along lines 31-31 of FIG. 29;

FIG. 34 is a perspective view of a sixth embodiment of the apparatus of the present invention;

FIG. 35 is a sectional view taken along lines 35-35 of FIG. 34; and

FIG. 36 is a sectional view of the sixth embodiment of the apparatus of the present invention.

DETAILED DESCRIPTION OF THE INVENTION

Figure 1:
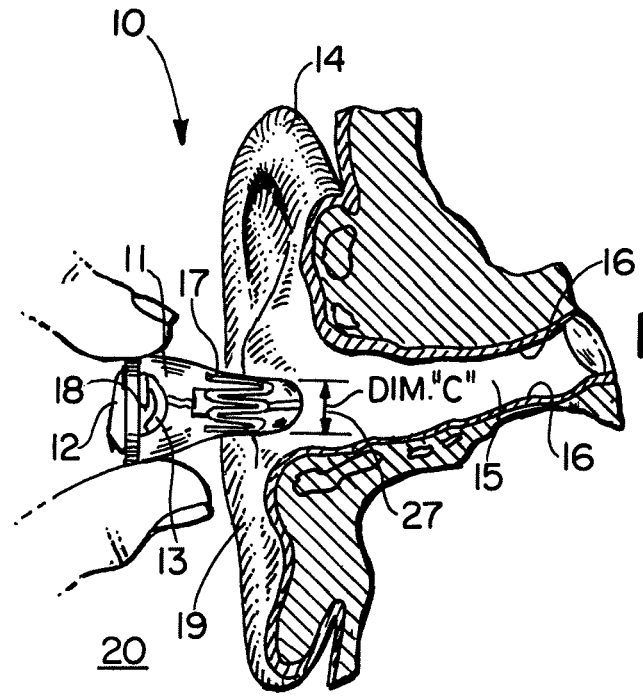
FIG. 1 is a sectional view of the external ear canal of a wearer, wherein the out-of-ear embodiment of the in-the-ear device is in the malleable Martensite state which is deformed by bias spring to its smaller size, the device being easily inserted through the bends of the wearer's ear canal.
Figure 2:
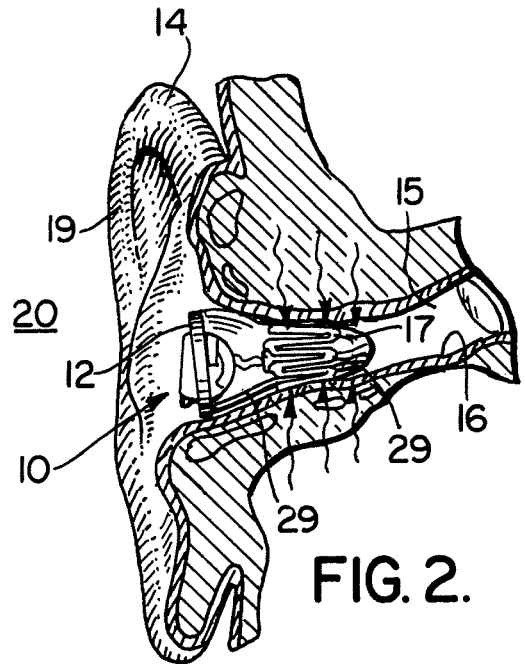
FIG. 2 is a perspective view of the preferred embodiment of the apparatus of the present invention shown positioned in the external ear canal thereby being exposed to body heat causing transformation from the Martensite phase to the Austenite Start (As) that starts recovery from the deformed shape to its annealed shape.
Figure 3:
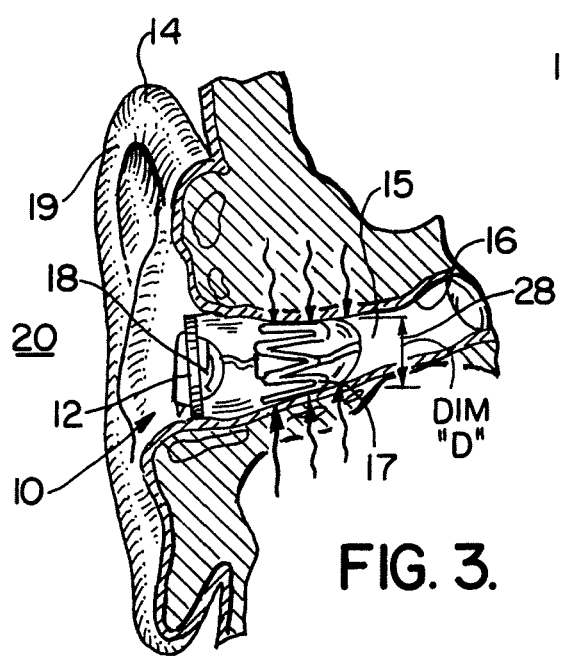
FIG. 3 is a perspective view of the preferred embodiment of the apparatus of the present invention shown in the recovered Austenite Finish (Af) state that transmits a radial force through the silicone body to the external ear canal wall yielding a comfortable, secure acoustic seal, free from acoustic feedback.

FIGS. 1-3 show generally the preferred embodiment of the apparatus of the present invention, designated generally by the numeral 10. Hearing device 10 has an internal stent or frame 17 that expands to its pre-molded state at human body temperature. In FIGS. 1-3 the practical application of apparatus 10 is an in the ear worn hearing aid, an active hearing protector, or a combination hearing protector hearing device, a passive hearing protector, a communication device, or a combination communication hearing and hearing protector device, or any combination sub-miniaturized into a single unit. As used herein, the term "hearing aid" is broadly construed to cover any of the above devices. Dim. C (arrow 27) of FIG. 1 is the smallest diameter of the device 10 in the malleable Martensite phase. The Nitinol preferably used to construct stent 17 will preferably reside in this state at typical room temperature below 30° C. The same malleable state may exist in the absence of a power signal for electrically driven stents. Illustrated by Dim. D (arrow 28) of FIG. 3 is the pre-molded diameter of the stent 17 for temperatures at or above 35° C. or when activated by an electrical signal for the active stents. Once completely inserted into a patient's ear canal 15 and expanded in the external ear canal 15, the device 10 achieves a precise peripheral seal with ear canal 15 wall 16 as shown in FIG. 3.

The hearing aid device 10 of FIG. 1 is characterized by a preferably flexible body 11 of soft silicone or other soft material compatible with ear canal 15 tissue. Hearing aid components 13 are also contained in body 11 and can include the battery compartment 18, the battery contacts and wire connections. Other hearing aid components 13 can include for example a microphone, a receiver, a transceiver, an electromagnetic coil, or a circuitry transceiver electromagnetic coil. Vent tube 29, extends through hearing aid 10 including body 11 and faceplate 12.

The pinna 19, external ear canal wall 16 and ear canal cavity 15 define the typical human ear. The outside environment (depicted by the numeral 20 in FIGS. 1-3) is room temperature for the preferred embodiment. Body heat shown in FIGS. 1, 2 and 3 transforms the stent from its smaller or deformed size (FIG. 1) to its original pre-molded shape memory size (FIG. 3). The flexible (e.g. silicone) body 11 may act as a bias spring to return the stent 17 to a deformed state when the device 10 has been removed from the ear and exposed to room temperature. Re-insertion of the device 10 into the ear canal 15 returns the device 10 to its original design shape. This property enables ready wear devices to self form to many individual ear canal 15 shapes without the logistics of an ear impression from which to custom mold the device form for that individual ear canal.

Figure 4:
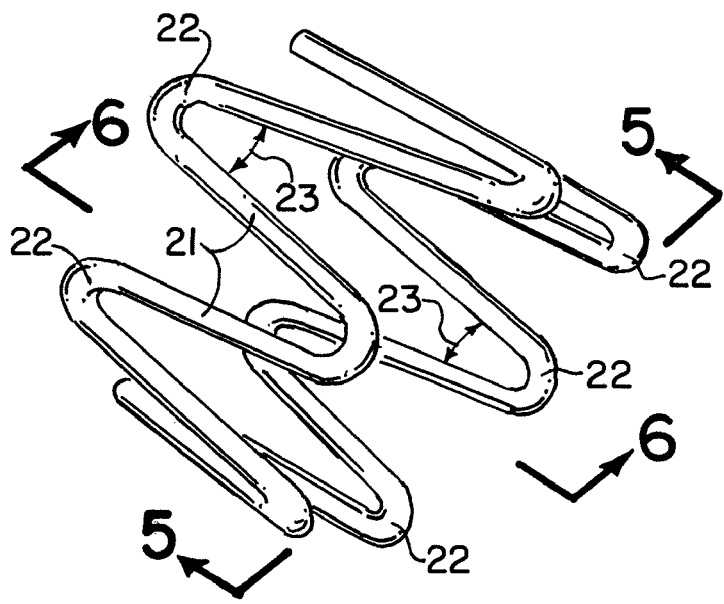
FIG. 4 is a perspective view of the preferred embodiment of the apparatus of the present invention showing the Nitinol stent portion that is in its molded state in the Austenite finish thus demonstrates the expanded size as shown in the device of FIG. 3.
Figure 5:
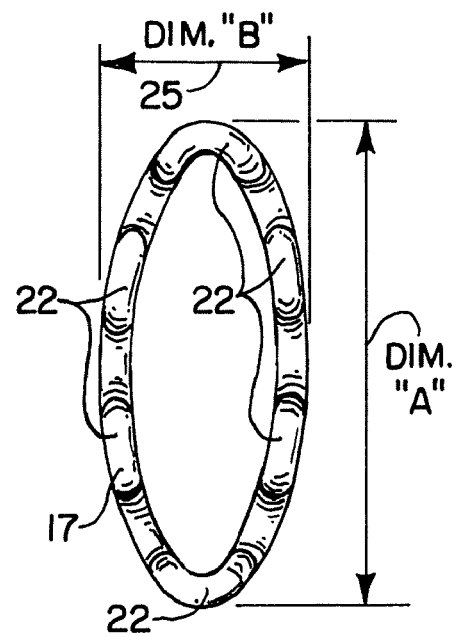
FIG. 5 is an end view of the stent, taken along lines 5-5 of FIG. 4, wherein dimension (Dim.) A is in the major axis and dimension (Dim.) B is the minor axis.
Figure 6:
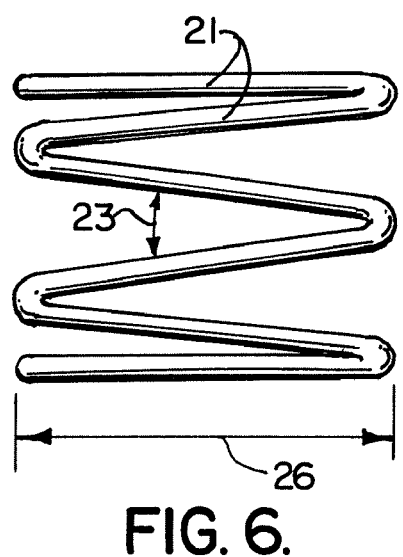
FIG. 6 is a side view of the preferred embodiment of the apparatus of the present invention showing a Nitinol stent that is in its compressed or deformed state in the Martensite phase, the small size as in the device of FIG. 1.
Figure 10:
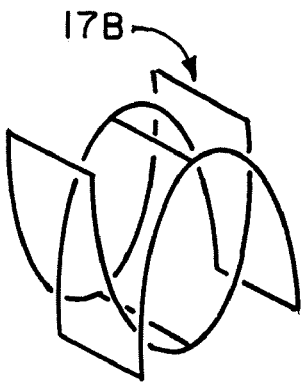
FIGS. 10-16 are perspective views of the preferred embodiments of the apparatus of the present invention showing various Nitinol stent designs that are in its molded state in the Austenite finish (the expanded size when in the device illustrated in FIG. 3)
Figure 11:
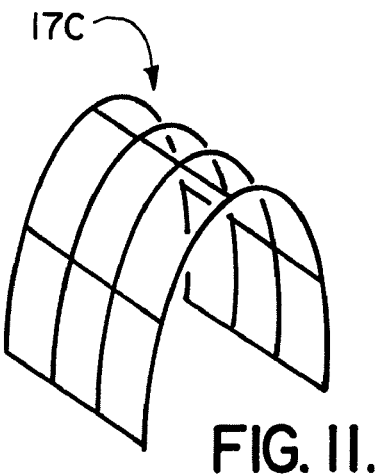

FIGS. 4-6 illustrate the Nitinol stent or frame 17 that can be micro-machined from a cylindrical tube, its preferred outer diameter (OD) FIG. 5 Dim. A (24) is 5-10 mm and Dim. B (25) is 3-9 mm viewed by 6. In FIGS. 4-6, stent 17 includes straight sections 21 connected with curved sections or bends 22. Angle 23 formed by two adjacent straight sections 21 can be between about 15 and 45 degrees. The overall longitudinal length 26 is preferred to be between about 4-8 mm. The cross sectional member depicted in FIG. 6 can be square, round, or rectangular. In the preferred embodiment the thickness is 0.0235 inches (0.0597 cm) each. The cross section may vary in shape and size depending on application and radial force requirements. The geometric angles forming the stent are defined are dependent on redial force requirements and additionally physical dimensions.

FIG. 7 illustrates a passive hearing protector or "ear plug" designated generally by the numeral 30. The faceplate 31 covering the proximal end of the device is typically plastic bonded to body 32. The silicone body 32 contains a conical or coil spring shape Nitinol spring 33. The device 30 is at room temperature 20 and is in the Martensite phase which is highly malleable. This embodiment would be elongated prior to insertion which reduces the cross sectional area for insertion. At body temperature the coil 33 will retract to its pre-molded austenite shape. In this simplest preferred embodiment illustrated in FIG. 7 in the invention utilizes a coil of similar shape to a spring in an inexpensive ink pen. This circular coil 33 can be extruded in memory metal. The coil 33 can then be shaped into a star configuration in the Martensite phase. This star shaped coil is then molded in a soft-solid silicone body 32 with its electronic components if an active device. The coil 33, or endoskeleton, is placed in the ear worn device 30, such that its longitudinal axis is parallel to the longitudinal axis of the external ear canal or more specifically to the medial-lateral axis of the ear canal. No electronic components are placed between the endoskeleton the external ear canal wall.

In more complex applications, such as the case of hearing devices shown in FIG. 1, the hearing aid components such as a receiver or transducer is housed inside the endoskeleton. In the case of electromagnetic devices, the electromagnetic coil is suspended from a micro machined hinge and gear assembly from the inside diameter of the stent. In both cases, at ear temperature shape memory alloy stent expands outward into its original Austenite shape, causing the soft-solid body of the ear device to move outward into full contact with the ear canal wall of the external ear canal precisely and securely positioning the transducers.

FIG. 8 shows a combination hearing protection and communication device, designated generally by the numeral 34. This complex hearing amplification device 34 provides both a hearing protection device and a communication device housed in a soft body 35. Two transducers are used in concert with a two channel RF transceiver. The acoustic transducer 36 delivers sound from the hearing amplification circuitry 37 delivering processed outside environmental sound and from the two channel transceiver 38 to the ear drum. The stent 17 positions the acoustic transducer 36 aiming it at the ear drum 39. The receiver is usually placed lateral to the stent with a port tube 40 extending through the inside of the stent 17 for acoustic sound transmission. The accelerometer 41 is positioned between the outside diameter of the stent 17 and the ear canal wall 16, so that once the stent 17 expands the accelerometer 41 is mechanically engaged to the external ear canal 15 wall 16 allowing it to pick up the wearers voice signals via bone conduction and transmit the voice signals to the transceiver 38. An ultra low power two channel RF transceiver, such as the Gennum Corporation GA3272, optimizes wireless digital audio communication to compatible wireless sensor networks. This apparatus 34 would achieve hearing amplification and hearing protection if desired, as well as enabling voice transmission from the wearer to a communication device (e.g. telephone 42) channeling phone signals back to the ear drum by way of the hearing amplification circuitry 37 via the transceiver 38. The apparatus 34 of FIG. 8 would further serve to protect the hearing of the wearer by an acoustic seal and a limiting circuit in the hearing amplification circuit 37.

In another embodiment of the invention, a stent or skeleton 17A is formed by a series of ribs shown in FIG. 9 is formed by a connected spine, similar to a human rib cage. This horseshoe shaped cross sectional structure is extruded in memory metal. The individual horseshoe shaped elements 43 are connected together by a spine 44 enabling the configuration to act like a plumbing snake during compression i.e. insertion. The spine 44 also maintains the relative spacing of the individual horseshoe shaped elements 43. This ribbed skeleton 17A is then molded in a soft body 12 with its electronic components 13. The skeleton 17A is located medially between the receiver and the proximal end of the soft device. This ear worn device's longitudinal axis is parallel to the longitudinal axis of the external ear canal 15 or more specifically to the medial-lateral axis of the ear canal 15. No electronic components are placed between the endoskeleton and the external ear canal wall. During expansion, pressure is developed on the anterior and posterior surfaces of the ear canal wall. The superior and inferior surfaces are maintained so that at ear temperature, said skeleton expands outward into its original horseshoe shape, causing the soft-solid body of the ear device to move outward into full contact with the ear canal wall of the external ear canal.

In FIGS. 10-16 various shapes and actions of the stent (designated respectively as 17B, 17C, 17D, 17E, 17F) are shown that would anchor devices for numerous applications in different locations of the external ear canal 15. Any of the preferred geometric configurations of the endoskeleton can be designed and validated through the use of Finite Element Analysis (FEA) modeling. Finite element models are created by breaking the design into numerous discrete members. The models simulate the functionality and mechanical properties covering boundary conditions and the effects on elements such as fields of displacement, strains, stresses, temperatures, state variables, etc. Further, FEA will identify any design are process problems in the earliest time frame.

FIGS. 17-21 show an alternate construction for the nitinol stent, designated generally by the numeral 45. Stent 45 is tapered, being generally conically shaped as shown in FIGS. 17, 19-21. This tapered or conical shape enables the stent 45 and a hearing aid to which it is affixed (e.g. hearing aid 10) to snugly fit or conform to the ear canal 15 of a patient's ear 14 notwithstanding differences in the cross section of the ear canal from one patient or user to the next.

Figure 20:
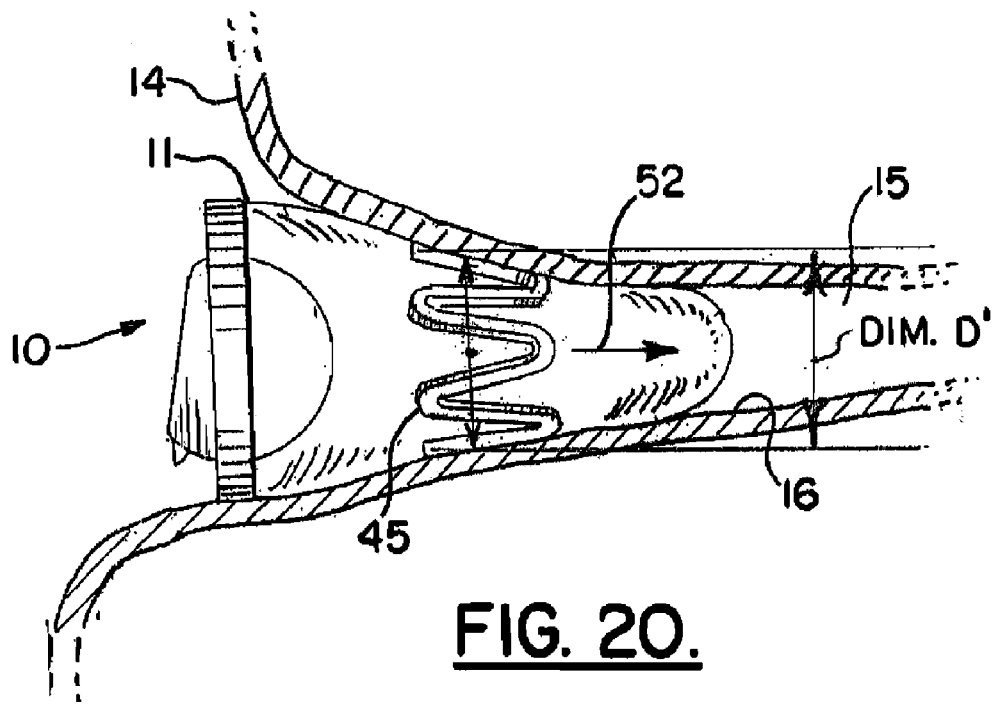
FIG. 20 is a sectional view of the external ear canal of a wearer containing hearing aid with the stent of FIGS. 17-19.
Figure 21:
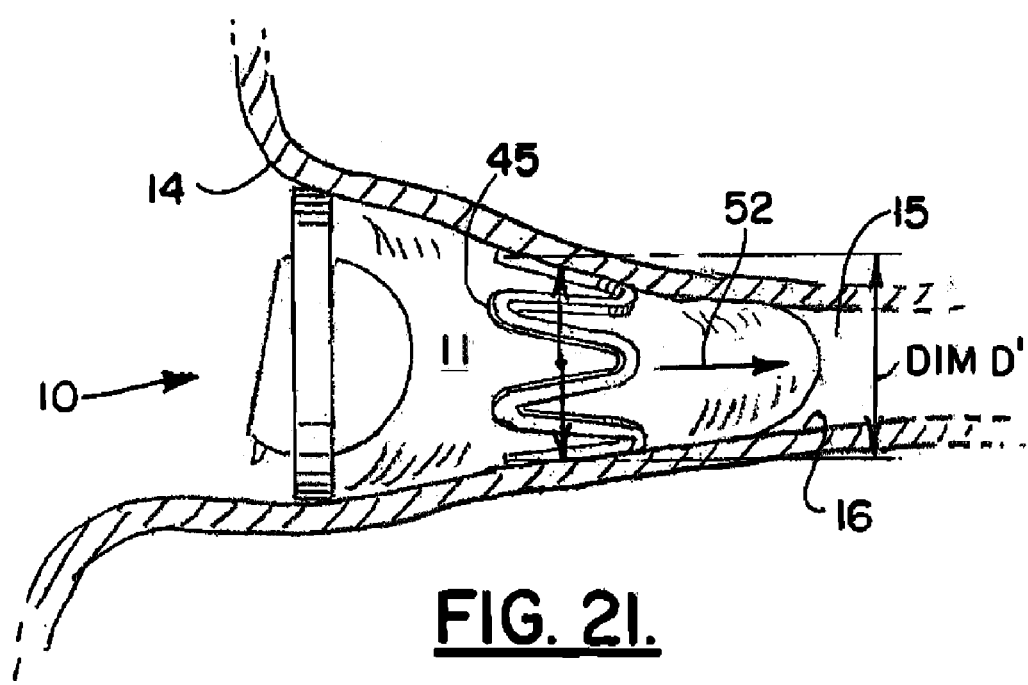
FIG. 21 is a sectional view of the external ear canal of a wearer wherein the ear canal is larger than the ear canal shown in FIG. 20.
Figure 22:
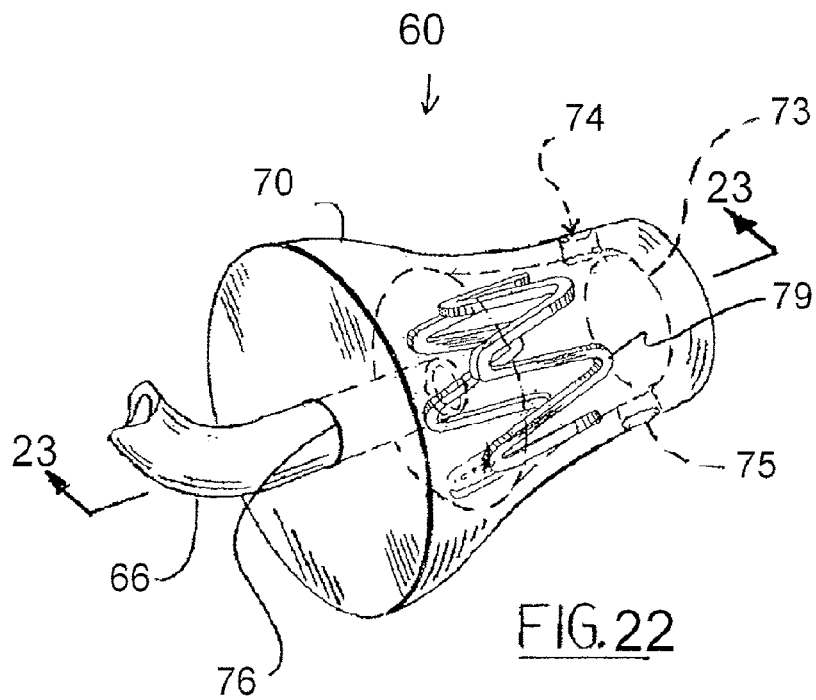
FIG. 22 is a fragmentary perspective view of a second embodiment of the apparatus of the present invention.
Figure 23:
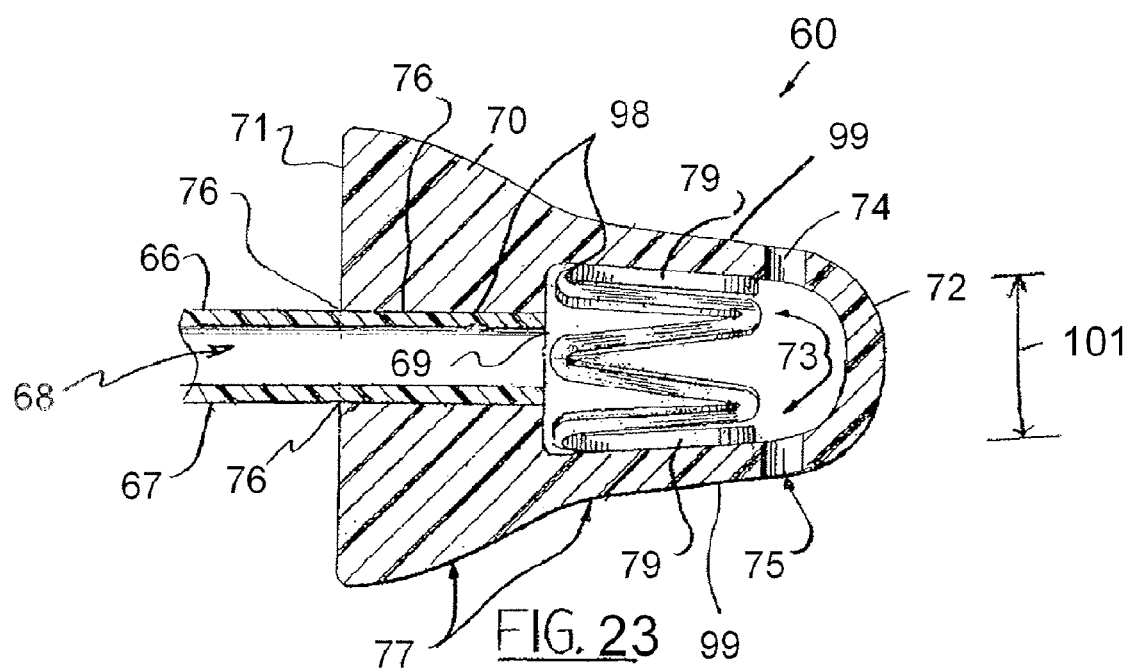
FIG. 23 is a fragmentary sectional view of the second embodiment of the apparatus of the present invention taken along lines 23-23 of FIG. 22.

In FIG. 20, the hearing aid 10 with stent 45 is shown fitting ear canal 15 of a patient's ear having a smaller ear canal. In FIG. 21, the ear canal 15 of the patient is larger. Because of the tapered or conical shape (which approximately matches the conical shape of the ear canal 15), the stent 45 will find its own snug position against the ear canal wall 16 as the patient or user pushes it inwardly in the direction of arrow 52 in FIGS. 20, 21 (thus, the hearing aid 10 seats deeper in the ear canal in FIG. 21 than in the ear canal in FIG. 20, but in each case it fits snugly against the ear canal 15 because of the tapered shape of stent 45). Dimension D' remains the same regardless of the size of the ear canal 15.

Figure 17:
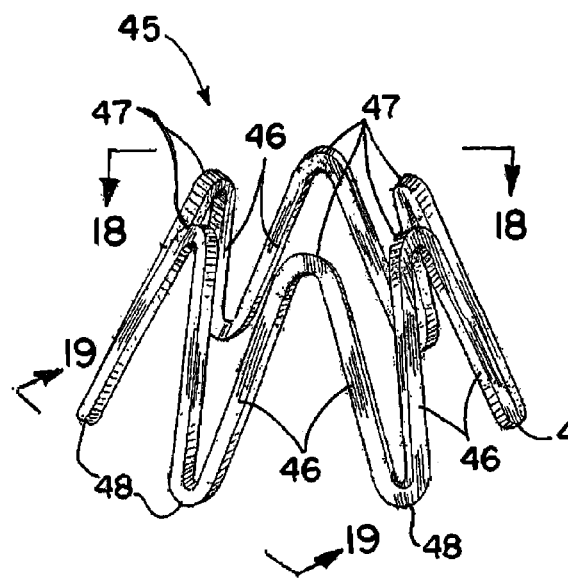
FIG. 17 is a perspective view of the preferred embodiment of the apparatus of the present invention showing an alternate construction for the Nitinol stent portion.
Figure 18:
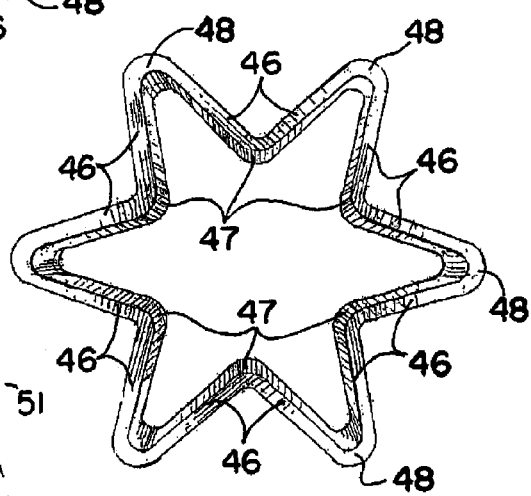
FIG. 18 is a sectional view taken along lines 18-18 of FIG. 17.
Figure 19:
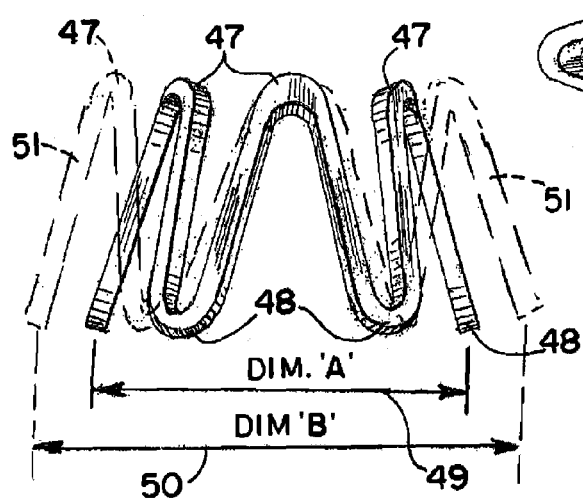
FIG. 19 is a sectional view taken along lines 19-19 of FIG. 17.

Stent 45 has a plurality of straight sections 46 connected with curved sections 47, 48 as shown in FIGS. 17-19. Dimension arrow 49 shows the initial position of stent 45 before insertion in the ear canal 15 of the user's ear 14. Once placed in the user's ear 14, stent 45 is warmed by the user's body temperature and the stent 45 expands. Arrow 50 schematically illustrates such expansion to a larger or greater dimension (see FIG. 19) designated by phantom lines 51.

In FIGS. 22-25, a second embodiment of the apparatus of the present invention is designated generally by the numeral 60. Hearing aid apparatus 60 provides an insert or plug 70 that is placed in the ear canal 63 of a user 61. A separate case or body 65 such as a behind-the-ear (BTE) type hearing aid case 65 is attached to the user's body. In the case of a behind the ear case 65, the case 65 is mounted to the user's ear 62 (preferably on the post auricular 64) as shown in FIG. 25.

The hearing aid case 65 (e.g. behind the ear hearing aid) contains known electronic hearing aid components 78 that generate audible sound or electronic signals. The audible sound can be transmitted via a hollow tube 16 to the insert or plug 70. Alternatively, in a second embodiment (FIGS. 26-27) electronic signals can be transmitted via a cable (e.g. wire) to the insert or plug 81 which carries a speaker or like electronic component capable of emitting sound that travels to the ear drum 97 of the user.

Tube 66 has a tube wall 67 that can be generally cylindrically shaped. Tube wall 67 surrounds tube lumen 68. Tube 66 is attached to case 65 or to any other sound generating device. Sound generated by case 65 and its electronic components 78 travels via tube 66 lumen 68 to tube end portion 69. Tube end portion 69 connects to insert or plug 70 at first end 71. Second end 72 of insert or plug 70 is that end closest to the user's ear drum 97 (see FIG. 36). Any type of connection can be made between tube wall 67 and insert or plug 70 such as an interference fit, adhesive connection, tied connection, fastened connection or the like.

Insert or plug 70 has a cavity 73. Cavity 73 carries stent 79. Cavity 73 also forms part of open ended channel 98. Sound port openings 74, 75 communicate between channel 98 and insert or plug outer surface 99. However, a single channel 113

(see FIG. 33) could be provided. Such a single channel 113 could be generally aligned with the central longitudinal axis of tube lumen 68. It should be understood that a combination of channels 74, 75, 113 could be used. An ear wax filter 114 (e.g. a foam layer) could be placed between any channel 74, 75, 113 and cavity 73 (see FIG. 33).

Tube receptive socket 76 is formed at first end portion of insert or plug 70. Tube 66 attaches to insert or plug 70 at tube receptive socket 76. Outer surface 99 of insert or plug 70 can include a tapered outer surface 77 that generally mimics the shape of the human ear canal. This tapered outer surface 77 can be provided in numerous shapes and sizes to enable a fit to most if not all users 61.

When a user 61 places insert or plug 70 in his or her ear canal 63 (see FIG. 25), the insert or plug 70 and its contained stent 79 are subjected to human body temperature. The stent 79 is preferably of a nitinol material that expands when a temperature at or near body temperature is reached. Thus, stent 79 begins with an initial average diameter of about 4 mm (see arrow 101, FIG. 23) and expands to a final average diameter of about 10 mm at the distal (larger) end of the stent and 6 mm at the proximal (smaller) end of the stent (next to the tympanic membrane). The expansion of stent 79 expands insert or plug 70 so that it conforms to the user's ear canal 100 (see FIGS. 26 and 36).

Figure 33:
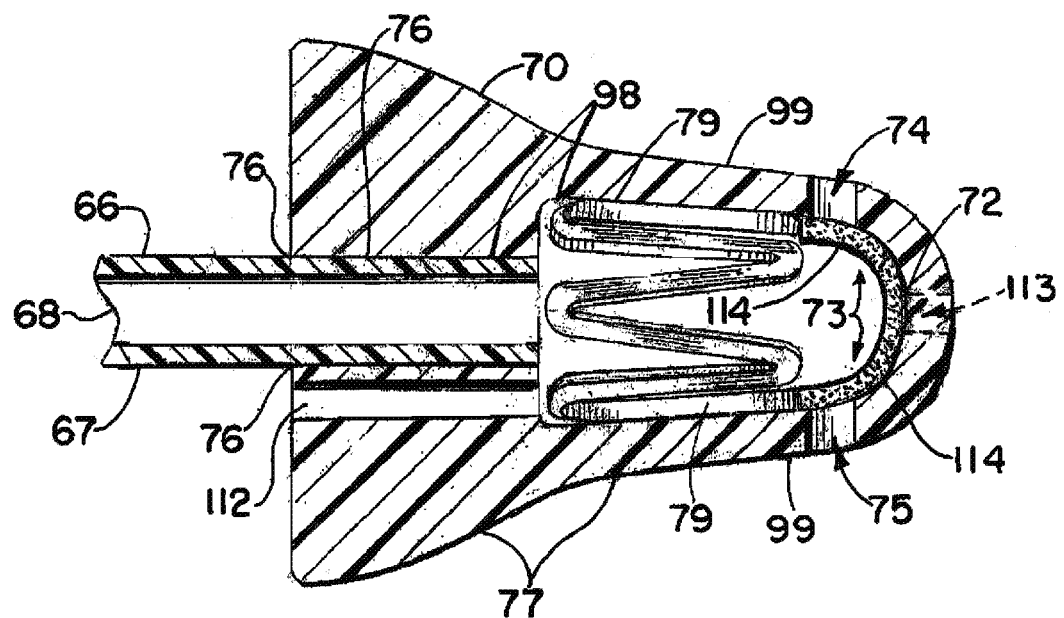
FIG. 33 is a sectional view of the fifth embodiment of the apparatus of the present invention.

A third embodiment of the apparatus of the present invention is shown in FIGS. 26-27, designated generally by the numeral 80. Hearing aid apparatus 80 provides an insert or plug 81 having a first end portion 82 and a second end portion 83. The second end portion 83 is positioned closest to a user's ear drum 97 when the insert or plug 81 is placed in the ear canal 63. Insert or plug 81 provides a cavity 84. A stent 79 is placed in cavity 84. Sound port openings 85, 86 communicate between the tapered outer surface 89 of insert or plug 81 and cavity 84. A third sound port opening such as 113 in FIG. 33 could be provided. Ear wax filter 114 could be provided between cavity 84 and any sound port opening 85, 86, 113 as shown in FIG. 33.

Socket 87 can be generally cylindrically shaped. The socket 87 extends between first end 82 of plug or insert 81 and cavity 84 as shown in FIG. 27. Socket 87 is receptive of speaker 88. The speaker 88 can be a commercially known speaker that is joined with wire cable 90 to a plug or connector 101 that enables an electronic connection to be made between speaker 88 and a selected sound generating device 100. The sound generating device 100 can be an Ipod®, MP3 player, Walkman®, CD player, radio electronic communication devices telemetry transponders, Blue Tooth transponders, or the like.

FIGS. 28-31 show yet another embodiment of the apparatus of the present invention designated generally by the numeral 91. Hearing aid apparatus 91 provides a band or banding 92 having an inner surface 93, outer surface 94, and band lumen 95. In FIGS. 28-31, the same tube 66 having wall 67 and tube lumen 68 is provided that is used with the preferred embodiment of FIGS. 22-25. It should be understood that the tube 66 of FIGS. 28-31 would connect to a hearing aid 65 such as the behind the ear type hearing aid shown in FIGS. 24 and 25. Tube 66 is joined to stent 79 with an appropriate connection 96 such as an adhesive connection, sonic weld, thermal weld, chemical weld, or any other means for attaching tube 66 to stent 79.

Banding 92 provides a wall 98. The wall 98 is dimensioned to provide sufficient space within band lumen 95 to receive stent 79 in a snug fitting relationship. The outer surface of stent 79 registers against and fits snuggly against the inner surface 93 of banding 92 when the stent 79 is outside the user's ear canal 63. When a user places the banding 92 with the contained stent 79 and attached tube 66 inside the ear canal 63, body temperature warms the stent 79 and causes it to expand, thus expanding the banding 92 so that it then fits snuggly against the ear canal 63 of the user.

Figure 32:
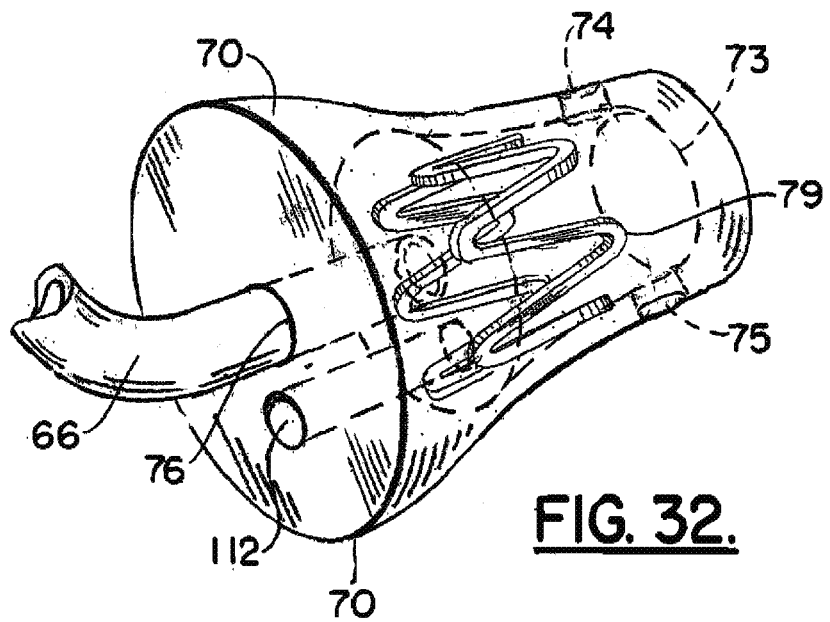
FIG. 32 is a perspective view of a fifth embodiment of the apparatus of the present invention.

FIG. 32 shows a fifth embodiment of the apparatus of the present invention that employs an optional vent tube 112. In FIG. 32, vent tube 112 extends between cavity 73 and first end 71 as shown. In all other respects, the embodiment of FIGS. 32-33 can be the same as the preferred embodiment of FIGS. 22-25.

FIGS. 34-36 show yet another embodiment of the apparatus of the present invention, designated generally by the numeral 102. Hearing aid apparatus 102 provides an insert or plug 103 having first end 104 and second end 105. The insert 103 provides a cavity 106 next to the second end 105 as shown in FIG. 33. A pair of sound port openings 107, 108 communicate sound between cavity 106 and the area outside of plug 103.

Socket 109 can be generally cylindrically shaped and is receptive of tubing 66. An interference fit can be used for example to attach tube 66 to socket 109. Alternatively, tube 66 can be attached to insert or plug 103 at socket 109 using adhesive or other means known in the art for joining a tube 66 to a polymeric or silicon body.

Figure 12:
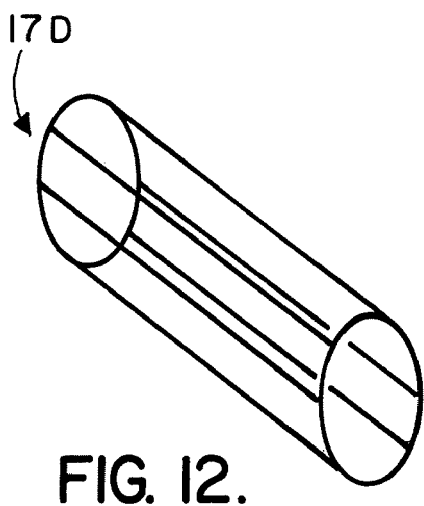
Figure 13:
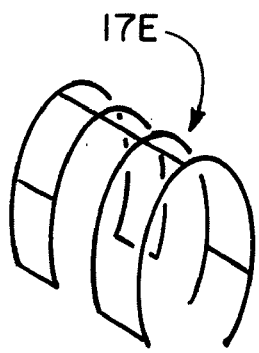
Figure 14:
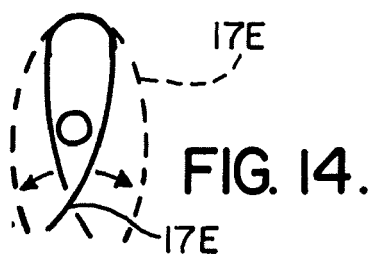
Figure 15:
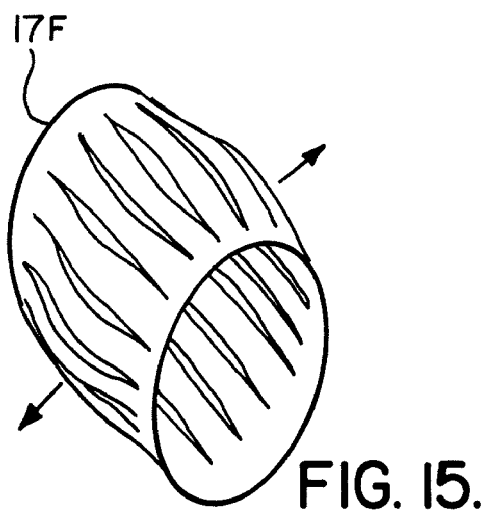
Figure 16:
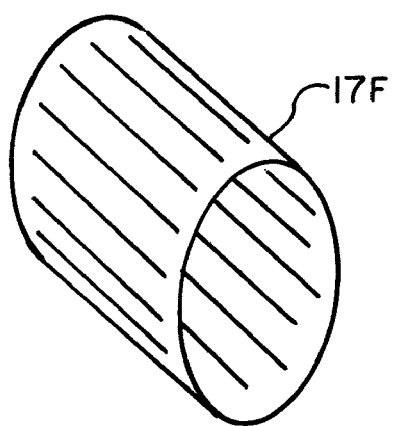

In FIGS. 34-36, a channel 111 extends from first end 104 of insert or plug 103 to cavity 106 as shown in FIG. 12. In the embodiment of FIGS. 34-36, a user 61 may be able to hear sounds of certain frequency without the aid of a hearing aid. Those sounds would thus travel to the wearer's ear drum 97 via channel 111 and cavity 106 and then sound port openings 107, 108. In the embodiment of FIGS. 32-34, sound of a frequency that the user does not hear can be transmitted from a hearing aid case 65 such as a known behind-the-ear or BTE type or other like device via tube 66 and its lumen 68 to cavity 106 and then to the user's ear drum 97 via sound port openings 107, 108 (or optionally a third port 113 as shown in FIG. 33).

As can be seen in FIG. 33, tube 66 can terminate adjacent the stent 79 or, as can be seen in FIG. 31, tube 66 can passes through the stent 79.

The following is a list of parts and materials suitable for use in the present invention.

| | PARTS LIST |
|---|---|
| Part Number | Description |
| 10 | hearing aid |
| 11 | flexible body |
| 12 | faceplate |
| 13 | hearing aid component |
| 14 | ear |
| 15 | ear canal |
| 16 | surface |
| 17 | nitinol stent |
| 18 | battery |
| 19 | pinna |
| 20 | outside environment |
| 21 | straight section |
| 22 | curved section |
| 23 | angle |
| 24 | dimension "A" |
| 25 | dimension "B" |
| 26 | length |
| 27 | arrow |
| 28 | arrow |
| 29 | vent tube |
| 30 | hearing protector |
| 31 | faceplate |
| 32 | soft, solid body |
| 33 | coil spring stent |
| 34 | hearing protection and communication device |
| 35 | body |
| 36 | acoustic transducer |

-continued

PARTS LIST

| Part Number | Description |
|---|---|
| 37 | circuitry |
| 38 | two channel transceiver receiver |
| 39 | ear drum |
| 40 | tube |
| 41 | accelerometer |
| 42 | mobile telephone |
| 43 | horseshoe shaped element |
| 44 | spine |
| 45 | Nitinol stent |
| 46 | straight section |
| 47 | curved section |
| 48 | curved section |
| 49 | dimension arrow |
| 50 | dimension arrow |
| 51 | expanded position |
| 52 | arrow |
| 60 | hearing aid apparatus |
| 61 | user |
| 62 | user's ear |
| 63 | ear canal |
| 64 | post auricular |
| 65 | behind the ear case |
| 66 | tube or conduit |
| 67 | tube wall |
| 68 | tube lumen |
| 69 | tube end portion |
| 70 | insert or plug |
| 71 | first end |
| 72 | second end |
| 73 | cavity |
| 74 | sound port opening |
| 75 | sound port opening |
| 76 | tube receptive socket or hollow bore |
| 77 | tapered outer surface |
| 78 | electronic components |
| 79 | stent |
| 80 | hearing aid apparatus |
| 81 | insert or plug |
| 82 | first end |
| 83 | second end |
| 84 | cavity |
| 85 | sound port opening |
| 86 | sound port opening |
| 87 | socket |
| 88 | speaker |
| 89 | tapered outer surface |
| 90 | wire cable or electronic conduit |
| 91 | hearing aid apparatus |
| 92 | banding |
| 93 | inner surface |
| 94 | outer surface |
| 95 | band lumen |
| 96 | connection |
| 97 | ear drum |
| 98 | wall |
| 99 | insert or plug outer surface |
| 100 | sound generating device |
| 101 | connector |
| 102 | hearing aid apparatus |
| 103 | insert or plug |
| 104 | first end |
| 105 | second end |
| 106 | cavity |
| 107 | sound port opening |
| 108 | sound port opening |
| 109 | socket |
| 110 | tapered outer surface |
| 111 | channel |
| 112 | vent tube |
| 113 | sound port opening |
| 114 | wax filter |

All of the above designs eliminate the need for component suspension since they are embedded in soft solid silicone throughout. Vent and sound bores are created by molding leaving a bore without wall space requirements.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A hearing aid comprising:
   a) a flexible plug that is sized and shaped to fit a user's ear canal;
   b) a stent embedded in the plug, the stent having a first smaller diameter at a temperature below body temperature and being expandable to a second greater diameter when subjected to the user's body temperature in the ear canal of the user;
   c) a hearing aid body containing electronic hearing aid components and that is selectively affixed to the user's body outside the ear canal;
   d) a conduit that connects the hearing aid body to the plug, the conduit enabling sound emitted by the hearing aid to travel via the conduit to the flexible plug so that the user is able to hear the sound received by the plug when the plug occupies the user's ear canal,
   wherein the conduit is a flexible tube, the tube has a central longitudinal lumen, and the tube terminates adjacent the stent.

2. The hearing aid of claim 1 wherein the plug has a hollow bore and the conduit occupies at least a part of the hollow bore.

3. The hearing aid of claim 1 wherein the stent is a nitinol stent.

4. The hearing aid of claim 1 wherein the stent is generally cylindrically shaped.

5. The hearing aid of claim 1 wherein the plug is of a polymeric material.

6. The hearing aid of claim 1 wherein the plug is of a silicone material.

7. The hearing aid of claim 1 wherein the hearing aid body is attachable to the user's outer ear.

8. The hearing aid of claim 1 wherein the hearing aid body has a speaker and the conduit affixes to the hearing aid body next to the speaker.

9. The hearing aid of claim 1 wherein the hearing aid body is a behind the ear configured hearing aid body.

10. The hearing aid of claim 1 further comprising a vent tube attached to the plug.

11. The hearing aid of claim 10 wherein the vent tube is mounted to an outer surface of the plug.

12. The hearing aid of claim 10 wherein the vent tube is embedded within the plug.

13. The hearing aid of claim 1 wherein the stent has a tapered shape.

* * * * *